(12) United States Patent
Rathschlag et al.

(10) Patent No.: US 7,365,109 B2
(45) Date of Patent: Apr. 29, 2008

(54) PIGMENT PREPARATION IN GRANULATE FORM

(75) Inventors: Thomas Rathschlag, Weilburg (DE); Sabine Schoen, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 444 days.

(21) Appl. No.: 10/380,404

(22) PCT Filed: Sep. 7, 2001

(86) PCT No.: PCT/EP01/10343

§ 371 (c)(1),
(2), (4) Date: Mar. 13, 2003

(87) PCT Pub. No.: WO02/22749

PCT Pub. Date: Mar. 21, 2002

(65) Prior Publication Data

US 2003/0176536 A1    Sep. 18, 2003

(30) Foreign Application Priority Data

Sep. 15, 2000    (DE) ................................ 100 46 152

(51) Int. Cl.
    *C09D 5/29*    (2006.01)
(52) U.S. Cl. ...................... 523/171; 524/430; 524/449; 524/492; 524/494; 524/497
(58) Field of Classification Search ................ 523/171; 524/449, 492, 497, 494, 430
    See application file for complete search history.

(56) References Cited

U.S. PATENT DOCUMENTS

| | | | | |
|---|---|---|---|---|
| 5,338,504 A | * | 8/1994 | Wang et al. ................ 264/555 |
| 5,401,313 A | * | 3/1995 | Supplee et al. ............... 106/12 |
| 5,455,288 A | * | 10/1995 | Needham .................... 523/205 |
| 6,291,412 B1 | * | 9/2001 | Kvita et al. .................. 510/301 |
| 6,398,862 B1 | * | 6/2002 | Hechler et al. ............. 106/404 |
| 6,432,195 B1 | | 8/2002 | Rathschlag et al. |
| 6,432,196 B1 | * | 8/2002 | Linde et al. ................. 106/712 |
| 6,544,327 B1 | * | 4/2003 | Griessmann et al. ........ 106/417 |
| 6,547,870 B1 | | 4/2003 | Griessmann et al. |
| 6,689,205 B1 | * | 2/2004 | Bruckner et al. ........... 106/415 |
| 6,702,885 B2 | * | 3/2004 | Schoen et al. ............. 106/31.9 |
| 6,972,305 B1 | * | 12/2005 | Griessmann et al. ........ 523/171 |

FOREIGN PATENT DOCUMENTS

| | | | |
|---|---|---|---|
| DE | 19618569 A1 | * | 11/1997 |
| DE | 19826624 | | 12/1999 |
| DE | 19929378 | | 12/2000 |
| DE | 19947175 | | 4/2001 |
| EP | 1153995 | | 11/2001 |
| SU | 445630 A | * | 10/1975 |
| WO | WO 01/74735 A1 | * | 10/2001 |

OTHER PUBLICATIONS

English Translation of SU 445630 (1975).*

* cited by examiner

*Primary Examiner*—Bernard Lipman
(74) *Attorney, Agent, or Firm*—Millen, White, Zelano & Branigan, P.C.

(57) ABSTRACT

The invention relates to pigment preparations in granulate form, containing one or more resins, one or more effect pigments and optionally, additives. The granulates are characterized in that they contain 3 to 10 wt. % water or a, solvent or solvent mixture with a vapor pressure of 0.001 to 40 hPa at 20° C.

17 Claims, No Drawings

PIGMENT PREPARATION IN GRANULATE FORM

The invention relates to pigment preparations in granule form comprising one or more resins, one or more effect pigments and, where appropriate, additives, the granules being notable for comprising 3-10% by weight of water or a solvent or solvent mixture having a vapour pressure at 20° C. of from 0.001 to 40 hPa.

In industrial processes, pigments are often not employed in the form of dry powders, since such powders produce dust, which leads to heightened requirements in terms of workplace safety. In many cases, furthermore, when introducing powders into plastics, basecoat systems, etc., agglomeration of the pigment powder is observed. Homogeneous distribution of the pigment in the respective matrix is frequently difficult if not impossible to achieve. In order to obtain the lustre effect typical of pearl lustre pigments in a formulation, extremely uniform distribution and orientation of the pearl lustre pigment particles in the binder is a necessity.

In applications, pigment granules feature a markedly reduced dust nuisance and better free-flow properties than pulverulent pigment preparations, and are therefore garnering increasing interest. The additional treatment of the pigments with a resin greatly enhances the performance properties of the pigments.

EP 0 134 676 B1 discloses a process for preparing non-dusting metal pigment compositions, in which the paste is prepared by mixing an organic binder medium and a metal pigment with an organic liquid vehicle. After the end of the preparation process, the organic liquid vehicle is removed from the coherent paste and the resulting solid mass is divided into particles.

Solvent-free, free-flowing granules comprising pearl lustre pigments and a binder and also additives, where appropriate, are claimed, furthermore, in EP 0 803 552 B1. The granules described therein are especially suitable as precursors for printing inks.

The prior art granules which have been largely freed from solvent during the preparation process, however, are comparatively difficult to dissolve again in the printing ink, and/or give rise to difficulties on dispersing. For the homogenization of the pearl lustre pigments from the granules in the formulation that is to be prepared, mechanical forces are required, which may in turn disrupt the platelets of the pearl lustre pigments, thereby adversely affecting the optical properties of the pigments.

It is an object of the present invention to provide effect pigment formulations in the form of solid particle forms which do not have the abovementioned disadvantages and which possess a markedly higher dissolution rate in binder systems than granules which have been largely freed from solvent.

It has surprisingly been found that the dissolution rate of granules comprising resins and effect pigments, such as pearl lustre pigments, for example, resins and, where appropriate, additives in printing inks or coating materials can be significantly increased if the granules are not freed completely from the solvent but instead still contain a precisely defined amount of solvent.

The invention accordingly provides pigment formulations in solid particle form comprising effect pigments, resins and, where appropriate, additives, characterized in that they contain 3-10% by weight, based on the granules, of a solvent which is non-volatile at room temperature. The chosen solvent or solvent mixture is selected so that it has a vapour pressure at 20° C. of from 0.001 to 40 hPa.

The granules of the invention are notable for an increased dissolution rate when incorporated by stirring into a binder system. Consequently, subsequent homogenization of the formulation that is to be prepared is made easier, since lower mechanical forces are needed to dissolve the granules. The introduction of foam into aqueous binder systems, and the risk of fracture of particularly coarse pigment fractions, are considerably reduced. Below the abovementioned solvent content (<3% by weight), the phenomenon occurs that the salvation or solubility of the granules, especially in solvent-containing and radiation-curing extenders, is greatly reduced. Moreover, the precise metering of the solvent content in the granules leads to better wetting of the pigment particles.

The granules of the invention are non-dusting, free-flowing, are much quicker to incorporate into commercially available binder systems than the prior art granules, and are compatible in the said systems. In particular the products are compatible with aqueous, solvent-containing and solvent-free printing ink and coating systems. The inks and coating materials prepared using the granules are suitable for gravure printing, flexographic printing, screen printing, offset overprint varnish (OPV) and also for the various coating systems in the industrial coating and automotive coating sectors. They are also suitable for colouring plastics.

The pigment granules of the invention contain $\geq 60\%$ by weight, preferably 70-90% by weight, in particular 80-90% by weight, of effect pigments. Very particular preference is given to pigment preparations having an effect pigment content of more than 80% by weight. The percentages by weight are always based on the granules.

The effect pigments referred to here are pearl lustre pigments, metallic effect pigments, multilayer pigments with transparent and opaque layers, holographic pigments, BiOCl and LCP (liquid crystal polymer) pigments.

Particular preference is given to granules comprising pearl lustre pigments based on platelet-shaped, transparent or semi-transparent substrates. Examples of suitable substrates are phyllosilicates, such as natural or synthetic mica or other silicatic materials, talc, sericite, kaolin and $SiO_2$, glass, $TiO_2$, graphite and $Al_2O_3$ platelets. Examples of the platelet-shaped substrates are those coated with rare earth metal sulfides, such as $Ce_2S_3$, titanium suboxides, titanium oxynitrides, pseudobrookite, with coloured or colourless metal oxides, such as $TiO_2$, (rutile or anatase) $Fe_2O_3$, $Fe_3O_4$, $SnO_2$, $ZrO_2$, $SiO_2$, $Al_2O_3$, $Cr_2O_3$, ZnO, CuO, NiO, $Ce_2O_3$ and other metal oxides, alone or in a mixture, in one uniform layer or in successive layers (multilayer pigments). Pearl lustre pigments are known, for example, from German patents and Patent Applications 14 67 468, 19 59 998, 20 09 566, 22 14 454, 22 15 191, 22 44 298, 23 13 331, 25 22 572, 31 37 808, 31 37 809, 31 51 343, 31 51 354, 31 51 355, 32 11 602, 32 35 017 and P 38 42 330 and are available commercially, e.g. under the brand name Iriodin® from Merck KGaA, Darmstadt, Germany. Multilayer pigments based on mica are sold, for example, by Merck KGaA or by EM Industries under the brand name Timiron® Splendid Copper, Timiron® Splendid Gold, Timiron® Splendid Green, Iriodin® Solargold or Dichrona® Splendid. Particularly preferred are multilayer pigments based on mica having a $TiO_2$—$SiO_2$—$TiO_2$ layer sequence.

Particularly preferred pigment granules comprise $TiO_2$—, $Fe_2O_3$— or $TiO_2/Fe_2O_3$-coated mica, $Al_2O_3$ or $SiO_2$ platelets. The $SiO_2$ platelets may be coated, for example, as described in WO 93/08237 (wet-chemical coating) or DE-A 196 14 637 (CVD process). $Al_2O_3$ platelets are known, for example, from EP 0 763 573 A1. Platelet-shaped substrates coated with one or more rare earth metal sulfides are disclosed, for example, in DE-A 198 10 317.

Also suitable are metallic effect pigments, especially aluminium flakes modified for aqueous and solvent-containing systems, as sold by Eckart under the brand name Rotovario Aqua® or Stapa Hydroxale® for aqueous applications, and also Variocrom® and Paliocrom® pigments from BASF, including in particular those from the Laid-Open Specifications EP 0 681 009 A1, EP 0 632 110 A1, EP 0 634 458 A1, and also LCP pigments (liquid crystal polymers). Examples of suitable effect pigments from BASF are Variocrom ED 1478, Variocrom ED 1479 and Variocrom ED 1480. Likewise suitable, furthermore, are all holographic pigments known to the person skilled in the art, and also platelet-shaped pigments which have metal layers. Pigments of this kind are sold, among others, by Flex, for example, under the brand names Chromaflair Red/Gold 000, Chromaflair Gold/Silver 080, Chromaflair Green/Purple 190 and Chromaflair Silver/Green 060. The Chromaflair pigments with a particle size of about 11-13 µm consist of an opaque aluminium core and a magnesium fluoride layer of varying thickness which generates the later interference colour of the resulting pigment. Additionally, a semi-translucent chromium layer is applied as the outermost layer.

The pigment granules of the invention may comprise one or more effect pigments. In many cases it is possible by using at least two different effect pigments to obtain special colour effects and lustre effects. Preferred pigment granules comprise one or two, or else three, effect pigments, especially those pigments which are based on mica and/or $SiO_2$ platelets. Also possible are blends of the effect pigments with organic and inorganic pigments at up to 10% by weight based on the granules, in which case the total amount of pigment ought not to exceed 90% by weight, based on the granules. Blending allows colour flops to be set in a very targeted way. In particular, the addition of one or more dyes and/or organic pigments in dispersed form leads to special colour effects. It is also possible to add those substances and particles (tracers) which enable the product to be identified.

As a mandatory component, the granules of the invention contain a resin or resin mixture in amounts of 4.5-30% by weight, preferably 4.5-25% by weight, in particular 4.5-20% by weight, based on the pigment granules. The acid number of the resin or resin mixture used is preferably from 90 to 350, in particular from 120 to 280 and, with very particular preference, from 150 to 270.

Suitable resins include all natural, semi-synthetic and fully synthetic resins or resin mixtures which are known to the person skilled in the art and in which effect pigments are commonly used. In particular, mention may be made here of ketone resins, aldehyde resins, cellulose and cellulose derivatives, such as alkylcellulose, hydroxycellulose, hydroxyalkylcellulose, cellulose acetobutyrate, cellulose nitrate, rosins, polyacrylate or polymethacrylate resins, alkyd resins, polyester resins, polyphenol resins, melamine resins, polyterpene, polyvinyl, polyvinyl chloride and polyvinylpyrrolidone resins, polystyrenes, polyolefins, epoxy resins, polyurethanes, urea, aromatic-formaldehyde resins, carbamic acid, sulfonamide and sulfo polyesters.

Particularly good dispersibility and redispersibility of the granules of the invention has been found if the resins used comprise modified rosins, especially styrene- and/or maleic-modified rosins, ketone and aldehyde resins, cellulose and/or cellulose derivatives, sulfo polyesters, styrene-modified maleates, polyacrylate resins or polymethacrylate resins, and styrene-modified polyacrylate resins. Particular preference is given to rosins which carry carboxyl groups, such as maleic- and fumaric-acid-modified rosins. Modified rosins are widely available on the market and are sold, for example, by Kraemer under the brand name Erkamar. Preference is also given to styrene-modified polyacrylate resins, sold for example under the brand name Morez by Morton.

A key constituent of the granules of the invention is the solvent or solvent mixture, which is present in amounts of ≧3% by weight, but at most up to 10% by weight, in the granules of the invention. The granules preferably contain 3-7.5% by weight, especially 3-5.0% by weight, of solvent, based on the granules. The solvent component in the granules must in each case be properly adapted to the resin system used. For preparation it is possible to use water and also all non-volatile organic solvents. Examples of suitable solvents are aromatic solvents, e.g. toluenes, petroleum spirits, xylenes, mineral oils, vegetable oils, glycol ethers, such as propylene glycol monoethyl ether, propylene glycol monoethyl ether or diols, such as ethylene glycol and propylene glycol or polyether diols, aliphatic triols and tetraols having from 2 to 6 carbon atoms, such as trimethylolethane, trimethylol-propane, glycerol, 1,2,4-butanetriol and 1,2,6-hexanetriol, alcohols, ketones, esters, and all other solvents from other classes of compound, or a mixture of two or three of the aforementioned solvents.

Particular preference is given to solvents having a boiling point >35° C., especially >70° C. It is preferred to use those solvents which are of medium or high viscosity. Particular preference is given to solvents which are readily miscible with water. It is important that during the preparation the solvent component includes at least one solvent or solvent mixture which has a vapour pressure at 20° C. of from 0.001 to 40 hPa, preferably from 0.001 to 30 hPa.

Particularly preferred solvents are water, polyalkylene glycol, glycol ethers, diols, aliphatic triols having 2-6 carbon atoms, glycerol, 1,2,4-butanetriol, 1,2,6-hexanetriol or a mixture of two or three of the aforementioned solvents. The vapour pressures of the suitable solvents may easily be determined by the person skilled in the art or looked up in the Handbook of Chemistry and Physics, 71st Edition, 1990-1991, David R. Lide, CRC Press, chapter 6-48.

Particular preference is given to polyalkylene glycols, toluene (29 hPa), xylene (10 hPa), 1,2-ethanediol (0.053 hPa), 1,2,3-hexanetriol (0.01 hPa), 1,2,3-propanetriol (0.001 hPa), and water (23 hPa). The water may also contain dissolved sorbitol or urea. Preferred polyalkylene glycols are polyethylene glycol (0.1 hPa) and ethylene glycol monobutyl ether (0.8 hPa) (vapour pressures at 20° C. indicated in brackets in each case are from the Handbook of Chemistry and Physics).

As a further component, the granules preferably comprise one or more neutralizing agents. Particularly suitable agents are the bases common in the coatings sector, such as urea, urea derivatives, ammonia, amino alcohols, such as 2-amino-2-methyl-1-propanol, alkali metal hydroxides, such as KOH or NaOH, amines, the latter in the case of granules for aqueous applications preferably being organic amines of low molecular mass which are non-volatile or possess a low volatility at room temperature.

In general, the pigment granules of the invention contain from 0.05 to 10% by weight of neutralizing agent, preferably from 1 to 7% by weight, in particular from 1.5 to 5% by weight, based on the pigment granules.

The granules of the invention may further comprise a modifier, as a further component, in amounts of from 0.05 to 10% by weight, preferably from 0.05 to 6% by weight, in particular from 0.05 to 3% by weight. The modifier used is in particular a polyalkylene oxide or polyalkylene oxide derivative, whose purpose is to enhance the strength of the granules and also their compatibility.

If necessary, the addition of a redispersing agent in the form of bulky particles, such as fibres or spherical particles, for example, prevents the effect pigments treated in accordance with the process of the invention from lying on top of one another to a notable extent as a result of steric repulsion and so exerting strong adhesion. The effect of this is that the granules of the invention are more stable and the effect pigments, after the granules have been introduced into the paint, printing ink or coating system, settle more slowly—in some cases very much more slowly—and the sediment is in any case less hard, and that no problems occur when the sediment is reagitated.

The redispersing agent is used preferably in amounts of from 0 to 5% by weight, in particular from 0.05 to 3% by weight, based on the granules. All organic and inorganic fibres having a fibre length of 0.1-20 µm that are known to the person skilled in the art may be used. Suitable particles are, in particular, all synthetic fibres, e.g. those of polyethylene, polyacrylates, polypropylene, polyamides, cellulose fibres, inorganic fibres, including preferably silicon compounds, glass fibres and also, in particular, the condensation products of modified isocyanates and mono- and diamines. These condensation products, comprising diurea derivatives and also amino ureas containing urethane groups, are known as thixotropic agents and together with a binder are added to paints and coating materials in order to improve the running properties and the brushability.

As redispersing agents it is also possible to use all diurea derivatives and urethane compounds that are known to the person skilled in the art, as are described, for example, in EP 0 198 519 and in Organic Coatings: Science and Technology, A. Heenriga, P. J. G. von Hemsbergen, pp. 201-222, New York 1983.

Particularly suitable spherical materials are hollow glass, wax or polymer beads made of vinyl resins, nylon, silicone, epoxy resins, olefin resins, polystyrenes, and inorganic materials, such as $TiO_2$, $SiO_2$ or $ZrO_2$, for example. It is preferred to use hollow beads, but also solid beads, having a particle size of from 0.05 to 150 µm. In the granules of the invention it is particularly preferred to use hollow glass, wax or polymer beads.

Spherical particles based on $SiO_2$ in a particle range of 3-10 µm are known, for example, as materials for high-performance liquid chromatography and are sold, for example, as LiChrospher® by Merck KGaA, Darmstadt, FRG. Such materials are preferably used in monodisperse form; that is, with a substantially uniform particle size. Monodisperse spherical particles of this type based on $SiO_2$, $TiO_2$ and $ZrO_2$ are known. Monodisperse $SiO_2$, for example, may be prepared in accordance with EP 0 216 278 B1. Hollow glass beads are sold, for example, under the trade name Q-CEL by PQ Corporation, USA, or Scotchlite by 3M, Frankfurt, FRG.

Additionally, the granules of the invention may comprise surface-active substances, such as alkylsilanes, for example, which may also contain a further functional group, or saturated or unsaturated fatty acids or fluorosurfactants. Particular preference is given to using silane compounds of the formula $(C_nH_{2n+1})Si(OC_mH_{2m+1})_3$, where n is 1-30 and m is 1-10, as surface-active substances. Examples of suitable silane compounds are n-hexyldecyltriethoxysilane and n-octyl-decyltriethoxysilane (Si 116 and Si 118 from Degussa AG, Frankfurt) and also the corresponding fluoroalkyl-silanes.

As surface-active substances it is also possible to use the saturated and unsaturated fatty acids, such as caproic acid, caprylic acid, capric acid, lauric acid, myristic acid, palmitic acid, stearic acid, oleic acid and linoleic acid, for example, and also fatty acid mixtures.

The surface-active reagent may also comprise a mixture of silane, fatty acids and/or surfactants. The granules may contain from 0.1 to 5% by weight, preferably from 0.2 to 3% by weight and in particular from 0.5 to 2% by weight of surface-active substances, based on the pigment.

For the preparation of the granules, the pigments, the resin and/or the resin mixture, and also the additives, where present, are mixed with the solvent. The fraction of the solvent at the beginning of the preparation is between 20-40% by weight, preferably between 25-35% by weight. During the preparation of the granules the resin and/or resin mixture and also optionally further additives are preferably premixed with the solvent before being added to the pigment. This produces intensive contact between pigment and the substances required for the granulation, which at the same time ensures more uniform covering of the pigment surface. Subsequently, this mixture is gently homogenized.

Preferably, the pigment is introduced as the initial charge and is first pasted up, with stirring, with the solvent containing the resin and, if desired at this stage, the modifier; subsequently, a further solution consisting of solvent and additives is added.

During or after its production, further customary additives may be added to this pigment preparation, examples being defoamers, wetting agents, anti-settling agents, levelling agents, emulsifiers, siccatives or thixotropic agents. These are auxiliaries which are customary in the coatings industry and may be present in the granules of the invention in an amount of from 0 to 10% by weight. Mention is made here in particular of succinate derivatives, examples being those as sold by Henkel under the brand name Hydropalat 875.

To prepare the granules, the moist pigment preparation is extruded or compacted into a compact particle form by other methods known to the person skilled in the art, such as by tableting, briquetting, pelletizing, granulating, spray-granulating or fluidized-bed granulating, and then dried under precisely controlled conditions. In the course of the drying operation, the solvent content of the granules is measured continuously. Depending on the solvent used, the drying process takes place at temperatures of from 60 to 150° C., preferably at from 60 to 120° C., and may where appropriate take place under reduced pressure, preferably at 80-100 mbar. The duration of drying depends on the batch size of the preparation to be dried, its throughput in the course of drying, and the solvent used, but is generally 0.5-24 h, preferably 1-18 h. As soon as the granules have a residual solvent moisture content of $\geq 3\%$ by weight, but $\leq 10\%$ by weight, the drying operation is halted. Finally, the granules are classified where necessary.

The term "granules" as used herein embraces all possible solid particle forms, such as pellets, chips, briquettes, tablets, etc. The particle sizes of the granules are situated within the range from 0.1 to 150 mm, preferably from 0.1 to 20 mm, in particular from 0.1 to 6 mm.

The determination of the residual solvent moisture content in the course of the preparation process takes place using a Sartorius MA 30 moisture analyzer, which works on an infrared basis. Following calibration, the water content is measured. Where further solubility enhancers are to be measured, this is done in accordance with the principle of differential weighing, since the substances to be analysed may be expelled together with the water above the previously calibrated temperature. There remains only the fraction of polymeric substance/resin and the effect pigment.

When measuring the water content using the Sartorious MA 30 moisture analyzer, the following parameters may be chosen in order to find the result:

| Initial sample mass: | 4-5 g of unground substance |
|---|---|
| Temperature: | 135-160° C. |
| Time setting: | 12-20 minutes |
| Result indication: | 0-100% (solvent content). |

The granules of the invention may be used for diverse applications. They are preferably used in coating systems from the sectors of printing, especially overprint varnishing, offset overprint varnishing, gravure, flexographic and screen printing. With particular preference, the granules as precursors for coating materials are applied to any desired substrate materials, examples being metals such as iron, steel, aluminium, copper, bronze, plastic, brass and also metal foils, and also glass, ceramic and concrete, and also wood, e.g. furniture, clay, textile, paper, packaging materials, e.g. plastic containers, films or boards, or to other materials for decorative and/or protective purposes. Furthermore, the granules of the invention are suitable in formulations for producing security features.

Accordingly, the invention also provides for the use of the granules of the invention in formulations such as paints, printing inks, security printing inks, coating materials, powder coating materials, coatings such as industrial and automotive coatings, in plastics, and in cosmetics.

The examples which follow are intended to illustrate the invention without, however, restricting it.

EXAMPLES

Example 1

1.1 Preparation of the Granulating Solution 260.0 g of DI water at 50° C. are introduced as an initial charge and 72 g of Rokramar 2150 granulating resin (modified rosin from Krämer) are incorporated by means of a 4-paddle stirrer. Then 17 g of 25% ammonia solution are added slowly and the mixture is stirred until the granulating resin has fully dissolved. Thereafter, 44 g of polyethylene glycol 1000 (from Merck KGaA) are added with stirring, followed by stirring for 5 minutes.

1.2 Preparation of the Granules

To prepare the granules, thorough mixing must be ensured. On the 1 kg scale, the mixture is prepared with the aid of an Eirich R02 mixer. 607 g of Iriodin® 231 (TiO$_2$/mica pigment of particle size 5-25 µm from Merck KGaA, Germany) are placed in the mixer vessel and 393 g of granulating solution from Example 1.1 are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 µm sieve. The solvent content of the granules in the drying process is measured continuously using the Sartorius MA 30 moisture analyzer. The following parameters were chosen in order to find the result:

| Initial sample mass: | 4-5 g of unground substance |
|---|---|
| Temperature: | 160° C. |
| Time setting: | 20 minutes |
| Result indication: | 0-100% (solvent content). |

The product is abrasion-resistant and dimensionally stable and is compatible, for example, with the customary solvent-free, free-radically UV-curing Rayoflex extender varnish, 11 HF 60 (UV varnish) from Hartmann Druckfarben and with the solvent-containing extender varnish Haptobond CT 105 (based on nitrocellulose with ethanol as solvent) from Hartmann Druckfarben. The granules thus prepared also exhibit a high dissolution rate when incorporated by stirring into the said printing ink systems.

Example 2

2.1 Preparation of the Granulating Solution 256.4 g of DI water at 50° C. are introduced as an initial charge and 66 g of Morez 300 granulating resin (polyacrylate resin from Morton) are incorporated by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added with stirring, followed by stirring at 300 rpm for 5 minutes.

2.2 Preparation of the Granules 597 g of Iriodin® 231 (TiO$_2$/mica pigment of particle size 5-25 µm from Merck KgaA) are placed in the mixer vessel and 403 g of granulating solution are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 µm sieve. The solvent content of the granules in the drying process is measured continuously using the Sartorius MA 30 moisture analyzer. The following parameters were chosen in order to find the result:

| Initial sample mass: | 4-5 g of unground substance |
|---|---|
| Temperature: | 135° C. |
| Time setting: | 12 minutes |
| Result indication: | 0-100% (solvent content). |

The granules obtained possess a residual moisture content of approximately 4±0.5% by weight and are abrasion-resistant, dimensionally stable, compatible, and also readily soluble in the aqueous offset overprint varnish 350081 from Weilburger Lackfabrik.

Example 3

3.1 Preparation of the Granulating Solution 256.4 g of DI water at 50° C. are introduced as an initial charge and 66 g of Morez 300 granulating resin are incorporated by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added with stirring, followed by stirring at 300 rpm for 5 minutes.

3.2 Preparation of the Granules 597 g of Iriodin® 103 (TiO$_2$/mica pigment of particle size 10-60 µm, Merck KGaA, Darmstadt, Germany) are introduced and 403 g of granulating solution are slowly added. At a speed of 300-500 rpm, 19.5 g of Solcolor Green (CI PG 7) pigment preparation from MK Chemicals are added as well. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. This gives greenish pearl lustre granules having interesting colouristic properties. The granules thus prepared are first of all separated from their coarse fraction by passing them through a sieve of mesh size 2 mm and then from their fine fraction by classifying using a 400 µm sieve.

The product possesses a residual moisture content of 4±0.5% by weight and is abrasion-resistant, dimensionally stable, compatible, and also readily soluble in the common offset overprint varnish 350081 from Weilburger Lackfabrik.

Example 4

4.1 Preparation of the Granulating Solution 256.4 g of DI water at 50° C. are introduced as an initial charge and 66 g of Morez 300 granulating resin are incorporated by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added with stirring, followed by stirring at 300 rpm for 5 minutes.

4.2 Preparation of the Granules 597 g of Iriodin® 103 are placed in the mixer vessel and 403 g of granulating solution are slowly added. At a speed of 300-500 rpm, 19.5 g of Solcolor Yellow (CI PY 83) pigment preparation from MK Chemicals are added as well. The mixture is mixed homogeneously.

The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. This gives yellowish pearl lustre granules having interesting colouristic properties. The granules thus prepared are first of all separated from their coarse fraction by passing them through a sieve of mesh size 2 mm and then from their fine fraction by classifying using a 400 µm sieve. The granules possess a residual moisture content of 4±1% by weight and are abrasion-resistant, dimensionally stable, compatible, and also readily soluble in the common aqueous offset overprint varnish 350081 from Weilburger Lackfabrik.

Example 5

5.1 Preparation of the Granulating Solution 256.4 g of DI water at 50° C. are introduced as an initial charge and 66 g of Morez 300 granulating resin (polyacrylate resin from Morton) are incorporated by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added with stirring, followed by stirring at 300 rpm for 5 minutes.

5.2 Preparation of the Granules

To prepare the granules, thorough mixing must be ensured. On the 1 kg scale, the mixture is prepared with the aid of an Eirich R02 mixer. 597 g of Paliocrom® Gold L2002 from BASF AG are placed in the mixer vessel and 403 g of granulating solution are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 µm sieve.

The solvent content of the granules in the drying process is measured continuously using the Sartorius MA 30 moisture analyzer. The following parameters were chosen in order to find the result:

| | |
|---|---|
| Initial sample mass: | 4-5 g of unground substance |
| Temperature: | 135° C. |
| Time setting: | 12 minutes |
| Result indication: | 0-100% (solvent content) |

The granules obtained possess a residual moisture content of approximately 5±0.5% by weight and are abrasion-resistant, dimensionally stable, compatible, and also readily soluble in the aqueous offset overprint varnish 350081 from Weilburger Lackfabrik.

Example 6

6.1 Preparation of the Granulating Solution 260.0 g of DI water at 50° C. are introduced as an initial charge and 72 g of Rokramar 2150 granulating resin (modified rosin from Krämer) are incorporated by means of a paddle stirrer. Then 17 g of 25% ammonia solution are added slowly and the mixture is stirred until the granulating resin has fully dissolved. Thereafter, 44 g of polyethylene glycol 1000 (from Merck KGaA) are added with stirring, followed by stirring for 5 minutes.

6.2 Preparation of the Granules

To prepare the granules, thorough mixing must be ensured. On the 1 kg scale, the mixture is prepared with the aid of an Eirich R02 mixer. 607 g of Colorstream® Autumn Mystery (Fe$_2$O$_3$-coated SiO$_2$ platelet of particle size 5-40 µm from Merck KGaA, Germany) are placed in the mixer vessel and 393 g of granulating solution from Example 6.1 are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 µm sieve.

The product is abrasion-resistant and dimensionally stable and is compatible, for example, with the customary solvent-free, free-radically UV-curing Rayoflex extender varnish, 11 HF 60 (UV varnish) from Hartmann Druckfarben and with the solvent-containing extender varnish Haptobond CT 105 (based on nitrocellulose with ethanol as solvent) from Hartmann Druckfarben. The granules thus prepared also exhibit a high dissolution rate when incorporated by stirring into the said printing ink systems.

Example 7

7.1 Preparation of the Granulating Solution 256.4 g of DI water at 50° C. are introduced as an initial charge and 66 g of Morez 300 granulating resin (polyacrylate resin from Morton) are incorporated by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added to the granulating solution with stirring, followed by stirring at 300 rpm for 5 minutes.

7.2 Preparation of the Granules 597 g of Chromaflair Silver/Green 060 effect pigment from Flex (aluminium substrate with an $MgF_2$ layer and an outer Cr layer, of particle size 11-13 µm) are placed in the mixer vessel and 403 g of granulating solution from Example 7.1 are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 µm sieve. The solvent content of the granules in the drying process is measured continuously using the Sartorius MA 30 moisture analyzer. The following parameters were chosen in order to find the result:

| Initial sample mass: | 4-5 g of unground substance |
|---|---|
| Temperature: | 135° C. |
| Time setting: | 12 minutes |
| Result indication: | 0-100% (solvent content). |

The granules obtained possess a residual moisture content of approximately 4±0.5% by weight and are abrasion-resistant, dimensionally stable, compatible, and also readily soluble in the aqueous offset overprint varnish 350081 from Weilburger Lackfabrik.

Example 8

8.1 Preparation of the Granulating Solution 256.4 g of DI water at 50° C. are introduced as an initial charge and 66 g of Morez 300 granulating resin (polyacrylate resin from Morton) are incorporated by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added to the granulating solution with stirring, followed by stirring at 300 rpm for 5 minutes.

8.2 Preparation of the Granules 597 g of Variocrom ED 1478 from BASF AG are placed in the mixer vessel and 403 g of granulating solution are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 µm sieve.

The solvent content of the granules in the drying process is measured continuously using the Sartorius MA 30 moisture analyzer. The following parameters were chosen in order to find the result:

| Initial sample mass: | 4-5 g of unground substance |
|---|---|
| Temperature: | 135° C. |
| Time setting: | 12 minutes |
| Result indication: | 0-100% (solvent content). |

The granules obtained possess a residual moisture content of approximately 4±0.5% by weight and are abrasion-resistant, dimensionally stable, compatible, and also readily soluble in the aqueous offset overprint varnish 350081 from Weilburger Lackfabrik.

Example 9

9.1 Preparation of the Granulating Solution 256.4 g of DI water at 50° C. are introduced as an initial charge and 66 g of Morez 300 granulating resin (polyacrylate resin from Morton) are incorporated within 1 minute at 300 rpm by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added to the granulating solution with stirring, followed by stirring at 300 rpm for 5 minutes.

9.2 Preparation of the Granules 597 g of 610 0 010 Non-Leafing Silver (acrylic based) from Eckart (aluminium effect pigment of particle size $D_{50}=8$ µm) are placed in the mixer vessel and 403 g of granulating solution are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 µm sieve.

The solvent content of the granules in the drying process is measured continuously using the Sartorius MA 30 moisture analyzer. The following parameters were chosen in order to find the result:

| | |
|---|---|
| Initial sample mass: | 4-5 g of unground substance |
| Temperature: | 135° C. |
| Time setting: | 12 minutes |
| Result indication: | 0-100% (solvent content). |

The granules obtained possess a residual moisture content of approximately 4±0.5% by weight and are abrasion-resistant, dimensionally stable, compatible, and also readily soluble in the aqueous offset overprint varnish 350081 from Weilburger Lackfabrik.

Example 10

10.1 Preparation of the Granulating Solution 260.0 g of DI water at 50° C. are introduced as an initial charge and 72 g of Rokramar 2150 granulating resin (modified rosin from Krämer) are incorporated by means of a 4-paddle stirrer. Then 17 g of 25% ammonia solution are added slowly and the mixture is stirred until the granulating resin has fully dissolved. Thereafter, 44 g of polyethylene glycol 1000 (from Merck KGaA) are added with stirring, followed by stirring for 5 minutes.

10.2 Preparation of the Granules 607 g of Timiron® Splendid Gold from Merck KGaA or EM Industries (multilayer pigment based on mica with alternating $SiO_2$ and $TiO_2$ layers, of particle size 10-60 82 m) are placed in the mixer vessel and 393 g of granulating solution from Example 10.1 are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classifying using a 400 μm sieve. The solvent content of the granules in the drying process is measured continuously using the Sartorius MA 30 moisture analyzer. The following parameters were chosen in order to find the result:

| | |
|---|---|
| Initial sample mass: | 4-5 g of unground substance |
| Temperature: | 160° C. |
| Time setting: | 20 minutes |
| Result indication: | 0-100% (solvent content) |

The product is abrasion-resistant and dimensionally stable and is compatible, for example, with the customary solvent-free, free-radically UV-curing Rayoflex extender varnish, 11 HF 60 (UV varnish) from Hartmann Druckfarben and with the solvent-containing extender varnish Haptobond CT 105 (based on nitrocellulose with ethanol as solvent) from Hartmann Druckfarben. The granules thus prepared also exhibit a high dissolution rate when incorporated by stirring into the said printing ink systems.

Example 11

11.1 Preparation of the Granulating Solution 231.1 g of Eastek 1300 (30% sulfo polyester dispersion in water, pH=6; density: 1.08 g/cm$^3$; MFT: 12° C.) are introduced as an initial charge and 144.3 g of DI water are stirred in using a 4-paddle stirrer. This solution is used as a granulating solution to prepare effect pigment granules.

11.2 Preparation of the Granules 624.6 g of Iriodin® 231 from Merck KGaA are placed in the mixing vessel and 375.4 g of granulating solution from Example 11.1 are slowly added. The mixture is mixed homogeneously. The wetted mixture is granulated on a TR 01 granulating plate from Eirich. The wet, granulated mixture is dried in a fluidized-bed dryer at from 80 to 120° C. for 0.5-4 h, without going below a residual moisture content of 3% by weight. The granules thus prepared are first of all separated from their coarse fraction by passing them through a sieve of mesh size 2 mm and then from their fine fraction by classification using a 400 μm sieve.

The granules obtained are abrasion-resistant, dimensionally stable and compatible and also readily soluble in the aqueous offset overprint varnish 350081 from Weilburger Lackfabrik.

Example 12

Paint

Formulations consisting of 3.00% pigment granules from Example 1
1.50% Monastral green 6Y spec. (from Zeneca)
0.50% Cappoxyt yellow 4214 (from Cappelle)
0.03% FW 200 pigment black (from Degussa)
0.40% dollar aluminium Alpate 7620 NS (from Alcan Toyo Europe)

Remainder: Basecoat material with 19% solids content (acrylate-melamine) and diluent mixture.

Example 13

Plastic 1 kg of polystyrene granules are wetted uniformly in a tumble mixer with 5 g of adhesive. Then 42 g of granules from Example 6 are added and the components are mixed for 2 minutes. These granules are processed under standard conditions in an injection moulding machine to give small stepped plates measuring 4×3×0.5 cm. The stepped plates are notable for their lustre.

Example 14

Comparative

Comparison of the dissolution rates of dried granules with granules containing approximately 4% by weight of solvent in a gravure printing ink.

| Gravure printing ink | Granules from Example 1: <1% residual solvent content in the ready-to-print ink | Granules from Example 1: about 4% residual solvent content in the ready-to print ink |
|---|---|---|
| Haptobond F 105, 20% pigmented with granules from Example 1 | Dissolution rate >30 min | Dissolution rate <10 min |

| Gravure printing ink | Granules from Example 3: <1% residual solvent content in the ready-to-print ink | Granules from Example 3: about 4% residual solvent content in the ready-to-print ink |
|---|---|---|
| Senolith-WL overprint varnish, aqueous, 350081; 20% pigmented with granules from Example 3 | Dissolution rate >30 min | Dissolution rate 10 min |

| Gravure printing ink | Granules from Example 4: <1% residual solvent content in the ready-to-print ink | Granules from Example 4: about 4% residual solvent content in the ready-to-print ink |
|---|---|---|
| Senolith-WL overprint varnish, aqueous, 350081; 20% pigmented with granules from Example 4 | Dissolution rate >30 min | Dissolution rate <10 min |

Example 15

15.1 Preparation of the Granulating Solution 260.0 g of DI water at 50° C. are introduced as an initial charge and 72 g of Rokramar 2150 granulating resin (modified rosin from Krämer) are incorporated by means of a 4-paddle stirrer. Then 17 g of 25% ammonia solution are added slowly and the mixture is stirred until the granulating resin has fully dissolved. Thereafter, 44 g of polyethylene glycol 1000 (from Merck KGaA) are added with stirring, followed by stirring for 5 minutes.

15.2 Preparation of the Granules 607 g of Iriodin® 305 Solargold (multilayer pigment based on mica with $TiO_2/Fe_2O_3$ and $SiO_2$ layers, of particle size 10-60 μm, from Merck KGaA) are placed in the mixer vessel and 393 g of granulating solution from Example 15.1 are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated form their coarse fraction by passing them through a sieve of mesh size 2 mm and then from their fine fraction by classifying using a 400 μm sieve.

The product is drive-resistant [sic] and dimensionally stable and is compatible, for example, with the customary solvent-free free-radically UV-curing Rayoflex extender varnish, 11 HF 60 (UV varnish) from Hartmann Druckfarben and with the solvent-containing extender varnish Haptobond CT 105 (based on nitrocellulose with ethanol as solvent) from Hartmann Druckfarben. The granules thus prepared also exhibit a high dissolution rate when incorporated by stirring into the said printing ink systems.

Example 16

16.1 Preparation of the Granulating Solution 256.4 g of DI water at 50° C. are introduced as an initial charge and 66 g of Morez 300 granulating resin (polyacrylate resin from Morton) are incorporated by means of a 4-paddle stirrer. Then 36.6 g of 75% 2-amino-2-methyl-1-propanol solution are added slowly and the mixture is stirred until the granulating resin has fully dissolved. Thereafter, 44 g of polyethylene glycol 1000 are added to the granulating solution with stirring, followed by stirring at 300 rpm for 5 minutes.

16.2 Preparation of the Granules 597 g of Iriodin® 305 Solargold are placed in the mixer vessel and 403 g of granulating solution are slowly added. The mixture is mixed homogeneously. The wetted mixture is granulated on a TR 01 granulating plate from Eirich. The moist, granulated mixture is dried in a fluidized-bed dryer at from 80 to 120° C. for 0.5-4 h, without going below a residual moisture content of 3% by weight. The granules thus prepared are first of all separated form their coarse fraction by passing them through a sieve of mesh size 2 mm and then from their fine fraction by classifying using a 400 μm sieve.

The granules obtained are abrasion-resistant, dimensionally stable, compatible and also readily soluble in the aqueous offset overprint varnish 350081 from Weilburger Lackfabrik.

Example 17

Nail Varnish with Pigment Preparation in Granule Form for Solvent-based Applications

| Raw material (commercial designation) | INCI (international nomenclature of cosmetic ingredients) composition | [%] |
|---|---|---|
| Granules with Dichrona Splendid ® BR | (1) Granules comprising a $TiO_2$/mica pigment coated with Prussian Blue | 2.35 |
| Thixotropic nail varnish base 1348 | (2) Toluene, ethyl acetate, butyl acetate, nitrocellulose, tosylamide/formaldehyde resin, dibutyl phthalate, isopropyl alcohol, stearalkonium hectorite, camphor, acrylates copolymer, benzophenone-1 | 96.65 |
| Organic or inorganic colour pigment dispersion in nitrocellulose lacquer | | q.s. |

Sources:
Merck KGaA
International Lacquers S.A.

Preparation:

Introduce the nail varnish base and add the pigment granules with stirring. Leave to swell for 30 minutes and then stir at 1 000 rpm for 10 minutes.

With the preparation method described, the granules can be incorporated without problems.

Example 18

Shower Gel with Pigment Preparation in Granule Form for Water-based Applications

| Raw material (commercial designation) | | INCI (international nomenclature of cosmetic ingredients) composition | [%] |
|---|---|---|---|
| Phase A | | | |
| Granules comprising Timiron ® Splendid Green | (1) | Granules comprising a multilayer pigment coated with TiO$_2$ and SiO$_2$ | 0.18 |
| Keltrol T | (2) | Xanthan gum | 0.75 |
| Water, demineralized | | Aqua (water) | ad 100.0 |
| Phase B | | | |
| Plantacare 2000 UP | (3) | Decyl glucoside | 20.00 |
| Texapon ASV 50 | (3) | Sodium laureth sulfate, sodium laureth-8 sulfate, magnesium laureth-8 sulfate, sodium oleth sulfate, magnesium oleth sulfate | 3.60 |
| Bronidox L | (4) | Propylene glycol, 5-bromo-5-nitro-1,3-dioxane | 0.20 |
| Perfume oil Everest 79658 SB, dye solution | | Perfume | 0.05 |
| Phase C | | | |
| Citric acid monohydrate | (1) | Citric acid | 0.15 |
| Water, demineralized | | | 10.00 |

Preparation:

For phase A, incorporate the pigment granules into the water with stirring. Incorporation is unproblematic and the granules dissolved immediately on addition of water. Scatter in Keltrol T slowly, with stirring, and stir until it has dissolved. Add phases B and C in succession, with slow stirring until all of the components are homogeneously distributed. Adjust pH to 6.0-6.5.

Sources:
(1) Merck KGaA
(2) Kelco
(3) Cognis GmbH
(4) Haarmann & Reimer GmbH

The invention claimed is:

1. A pigment composition in granule form comprising:
a resin or resin mixture and
≧60% of one or more effect pigments,
wherein the granules comprise 3-10% by weight of water or a solvent or solvent mixture having a vapour pressure of 0.001-40 hPa (20° C.).

2. A pigment composition in granule form according to claim 1, wherein the solvent is water, polyalkylene glycol, glycol ether, a diol, an aliphatic triol having from 2 to 6 carbon atoms, glycerol, 1,2,4-butanetriol, 1,2,6-hexanetriol or a mixture of two or more of the said solvents.

3. A pigment composition in granule form according to claim 1, wherein the granules contain
≧4.5-30% by weight of resin or resin mixture based on the total weight of the granules.

4. A pigment composition in granule form according to claim 1, wherein the resin is an aldehyde or ketone resin, modified rosin, cellulose, cellulose derivative, sulfo polyester, polyacrylate resin, polymethacrylate resin or styrene-modified polyacrylate resin.

5. A pigment composition in granule form according to claim 1, wherein the resin or resin mixture has an acid number of 90-350.

6. A pigment composition in granule form according to claim 1, wherein the effect pigments are pearl lustre pigments, metallic effect pigments, multilayer pigments with transparent, or transparent and opaque, layers, holographic pigments, BiOCl or LCP (Liquid Crystal Polymer) pigments.

7. A pigment composition in granule form according to claim 6, wherein the pearl lustre pigments are based on mica, SiO$_2$, glass, TiO$_2$, or Al$_2$O$_3$ platelets.

8. A pigment composition in granule form according to claim 6, wherein the pearl lustre pigment is a mica, Al$_2$O$_3$ or SiO$_2$ platelet coated with TiO$_2$, Fe$_2$O$_3$ or TiO$_2$/Fe$_2$O$_3$.

9. A pigment composition in granule form according to claim 6, wherein the multilayer pigment is a mica platelet coated with TiO$_2$-SiO$_2$-TiO$_2$.

10. A pigment composition in granule form according to claim 1, wherein the granules further contain 0.05-10% by weight of a neutralizing agent, based on the total weight of the granules.

11. A pigment composition in granule form according to claim 1, wherein the granules further contain 0.05-10% by weight of a modifier, based on the total weight of the granules.

12. A pigment composition in granule form according to claim 1, wherein the granules further comprise defoamers, surface-active substances, wetting agents, anti-settling agents, levelling agents, desiccatives and/or thixotropic agents.

13. A pigment composition in granule form according to claim 1, further comprising additives.

14. A pigment composition in granule form according to claim 3, wherein the granules contain
≧4.5-20% by weight of resin or resin mixture, based on the total weight of the granules.

15. A pigment composition in granule form according to claim 5, wherein the resin or resin mixture has an acid number of 150 to 270.

16. A pigment composition in granule form according to claim 1, wherein the pigment composition has an effect pigment content of more than 80% by weight, based on the total weight of the granules.

17. A plastic, cosmetic, paint, varnish, powder coating material, printing ink, or a security printing ink composition comprising a pigment composition according to claim 1.

* * * * *